United States Patent [19]

Mongelli et al.

[11] Patent Number: 5,700,788
[45] Date of Patent: Dec. 23, 1997

[54] UREIDO DERIVATIVES OF NAPHTHALENEPHOSPHONIC ACIDS

[75] Inventors: Nicola Mongelli, Milan; Angelo Crugnola, Varese; Andrea Lombardi Borgia, Paullo; Enrico Pesenti, Cologno Monzese, all of Italy

[73] Assignee: Pharmacia & Upjohn S.p.A., Milan, Italy

[21] Appl. No.: 535,056

[22] PCT Filed: Feb. 8, 1995

[86] PCT No.: PCT/EP95/00444

§ 371 Date: Oct. 30, 1995

§ 102(e) Date: Oct. 30, 1995

[87] PCT Pub. No.: WO95/23806

PCT Pub. Date: Sep. 8, 1995

[30] Foreign Application Priority Data

Mar. 1, 1994 [GB] United Kingdom ............... 9403909

[51] Int. Cl.$^6$ .......................... A61K 31/675; C07F 9/572
[52] U.S. Cl. .............................. 514/91; 548/112
[58] Field of Search .................. 548/112; 514/91

[56] References Cited

U.S. PATENT DOCUMENTS

| | | | |
|---|---|---|---|
| 5,260,329 | 11/1993 | Mongelli et al. | 514/422 |
| 5,310,752 | 5/1994 | Lazzari et al. | 514/422 |
| 5,420,296 | 5/1995 | Mongelli et al. | 514/422 |
| 5,472,976 | 12/1995 | Animati et al. | 514/422 |
| 5,534,539 | 7/1996 | Mongelli et al. | 514/422 |

OTHER PUBLICATIONS

Cram and Hammond, "Organic Chemistry", Mc–Graw Hill Book Co., N.Y. (1964) 2nd Edition, pp. 565–567.

Antiviral Research 27 (1995) 335–354, "Novel sulfonated and phosphonated analogs of distamycin which inhibit the replication of HIV", David J. Clanton, Robert W. Buckheit, Jr., Sara J. Terpening, Rebecca Kiser, Nicola Mongelli, Andrea Lombardi Borgia, Robert Schultz, Ven Narayanan, John P. Bader and William G. Rice.

*Primary Examiner*—Patricia L. Morris
*Attorney, Agent, or Firm*—Oblon, Spivak, McClelland, Maier & Neustadt, P.C.

[57] ABSTRACT

Subject of the present invention are new ureido derivatives of naphthalenephosphonic acids having the following formula (I)

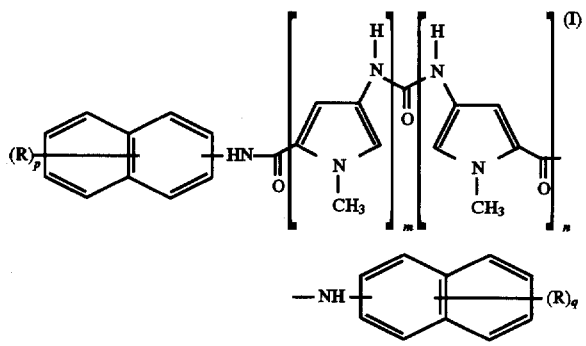

wherein each of m and n, which are the same, is an integer of 1 to 4; each of p and q, which are the same, is an integer of 1 to 3; and each of the R groups, which are the same, is a free or esterified phosphonic acid group; and the pharmaceutically acceptable salts thereof.

16 Claims, No Drawings

UREIDO DERIVATIVES OF NAPHTHALENEPHOSPHONIC ACIDS

This application is a 371 of PCT/EP95/0444, filed Feb. 8, 1995.

The present invention relates to new ureido derivatives of naphthalenephosphonic acids, to a process for their preparation, to pharmaceutical compositions containing them and to their use in medicine.

In international application PCT/EP91/00014 ureido derivatives of poly-4-amino-2-carboxy-1-methyl-pyrrole compounds are disclosed.

Now we have found that new naphthalenephosphonic acid derivatives and a narrow selected class of new naphthalenephosphonic acids falling within the scope of the general formula of PCT/EP91/00014, but therein not specifically disclosed, are endowed with valuable biological properties.

Accordingly, subject of the present invention are new ureido derivatives of naphthalenephosphonic acids having the following formula (I)

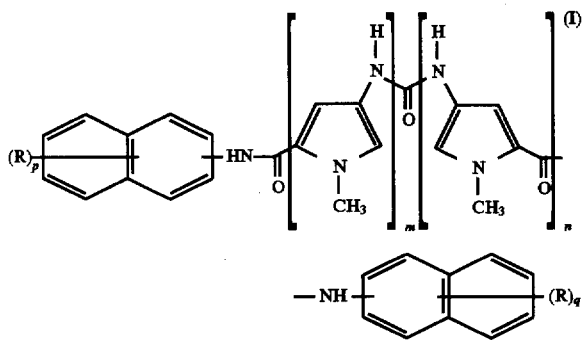

wherein
each of m and n, which are the same, is an integer of 1 to 4; each of p and q, which are the same, is an integer of 1 to 3; and each of the R groups, which are the same, is a free or esterified phosphonic acid group; and the pharmaceutically acceptable salts thereof.

The free, salified or esterified phosphono $(HO)_2PO$- groups may be on either or both the phenyl moieties of the naphthalene group.

The substituted naphthyl groups are preferably 1-, 2-, 3- or 4-naphthyl groups, typically 3- or 4-naphthyl groups. When the naphthyl groups are substituted by three free, esterified or salified phosphonic acid groups, the phosphonic acid substituents are preferably in the 1-, 5- and 7-, 2-, 5- and 6- or 2-, 5- and 7-positions. When they are substituted by 2 free, esterified or salified acid groups, the phosphonic acid substituents are preferably in the 1- and 5-, 1- and 6-, 1- and 7- or 5- and 7-positions. When they are substituted by one free, esterified or salified acid group, the phosphonic acid substituent is preferably in the 1-, 3-, 5- or 6-position. The invention also includes within its scope all the possible isomers, stereoisomers and their mixtures and the metabolites and the metabolic precursors or bio-precursors of the compounds of formula (I). As already said, the invention includes within its scope also the esters and the pharmaceutically acceptable salts of the acids of formula (I).

Only one or both of the two acidic functions of each phosphone $(HO)_2PO$-group can be salified and/or esterified.

In the salts of the invention preferably only one of the two acidic functions of each phosphono group is in a salified form, whereas in the esters of the invention both of the two acidic functions of each phosphono group are preferably in an esterified form.

Esters of the acids of formula (I) are for instance alkyl and aryl-alkyl esters, having a branched or straight alkyl chain. $C_1$–$C_6$ alkyl and phenyl-$C_1$–$C_6$ alkyl esters, typically methyl, ethyl, propyl, isopropyl, butyl, benzyl and phenylethyl esters, are more preferred.

Examples of pharmaceutically acceptable salts are either those with inorganic bases, such as sodium, potassium, calcium and aluminium hydroxides, or with organic bases, such as lysine, arginine, N-methylglucamine, triethyl-amine, triethanolamine, dibenzylamine, methylbenzylamine, di-(2-ethyl-hexyl)-amine, piperidine, N-ethylpiperidine, N,N-diethylaminoethylamine, N-ethylmorpholine, β-phenethylamine, N-benzyl-β-phenethyl-amine, N-benzyl-N,N-dimethylamine and the other acceptable organic amines. Sodium and potassium salts are preferred.

As stated above, the present invention also includes within its scope pharmaceutically acceptable bio-precursors (otherwise known as pro-drugs) of the compounds of formula (I), i.e. compounds which have a different formula to formula (I) above but which nevertheless upon administration to a human being are converted directly or indirectly in vivo into a compound of formula (I).

Preferred compounds of formula (I) are the compounds wherein each of m and n is 2; each of p and q is 2; and each of the R groups, which are the same, is a free or a $C_1$–$C_6$ alkyl- or phenyl-$C_1$–$C_6$ alkyl-esterified phosphonic acid group; and the pharmaceutically acceptable salts thereof.

Examples of preferred compounds of the invention are:
carbonylbis-3-({4-[(4-aminopyrrole-1-methyl-2-carbonyl) amino]-1-methylpyrrole-2-carbonyl}amino)-naphthalene-1,5-diphosphonic acid;
carbonylbis-4-({4-[(4-aminopyrrole-1-methyl-2-carbonyl) amino]-1-methylpyrrole-2-carbonyl}amino)-naphthalene-1,7-diphosphonic acid;
carbonylbis-3-({4-[(4-aminopyrrole-1-methyl-2-carbonyl) amino]-1-methylpyrrole-2-carbonyl}amino)-naphthalene-1,6-diphosphonic acid;
carbonylbis-4-({4-[(4-aminopyrrole-1-methyl-2-carbonyl) amino]-1-methylpyrrole-2-carbonyl}amino)-naphthalene-1,6-diphosphonic acid;
carbonylbis-3-({4-[(4-aminopyrrole-1-methyl-2-carbonyl) amino]-1-methylpyrrole-2-carbonyl}amino)-naphthalene-5,7-diphosphonic acid;
carbonylbis-2-({4-[(4-aminopyrrole-1-methyl-2-carbonyl) amino]-1-methylpyrrole-2-carbonyl}amino)-naphthalene-1,5-diphosphonic acid;
carbonylbis-1-({4-[(4-aminopyrrole-1-methyl-2-carbonyl) amino]-1-methylpyrrole-2-carbonyl}amino)-naphthalene-5,7-diphosphonic acid;
carbonylbis-4-({4-[(4-aminopyrrole-1-methyl-2-carbonyl) amino]-1-methylpyrrole-2-carbonyl}amino)-naphthalene-5,7-diphosphonic acid;
carbonylbis-1-({4-[(4-aminopyrrole-1-methyl-2-carbonyl) amino]-1-methylpyrrole-2-carbonyl}amino)-naphthalene-5,6-diphosphonic acid;
carbonylbis -4-({4-[(4-aminopyrrole-1-methyl-2-carbonyl) amino]-1-methylpyrrole-2-carbonyl}amino)-naphthalene-5,6-diphosphonic acid;
carbonylbis-4-({4-[(4-aminopyrrole-1-methyl-2-carbonyl) amino]-1-methylpyrrole-2-carbonyl}amino)-naphthalene-2,5-diphosphonic acid;
carbonylbis-4-({4-[(4-aminopyrrole-1-methyl-2-carbonyl) amino]-1-methylpyrrole-2-carbonyl}amino)-naphthalene-6,7-diphosphonic acid;

carbonylbis-4-({4-[(4-aminopyrrole-1-methyl-2-carbonyl) amino]-1-methylpyrrole-2-carbonyl}amino)-naphthalene-2,6-diphosphonic acid;

carbonylbis-4-({4-[(4-aminopyrrole-1-methyl-2-carbonyl) amino]-1-methylpyrrole-2-carbonyl}amino)-naphthalene-2,7-diphosphonic acid;

carbonylbis-1-({4-[(4-aminopyrrole-1-methyl-2-carbonyl) amino]-1-methylpyrrole-2-carbonyl}amino)-naphthalene-5-phosphonic acid;

carbonylbis-4-({4-[(4-aminopyrrole-1-methyl-2-carbonyl) amino]-1-methylpyrrole-2-carbonyl}amino)-naphthalene-5-phosphonic acid;

carbonylbis-4-({4-[(4-aminopyrrole-1-methyl-2-carbonyl) amino]-1-methylpyrrole-2-carbonyl}amino)-naphthalene-6-phosphonic acid;

carbonylbis-1-({4-[(4-aminopyrrole-1-methyl-2-carbonyl) amino]-1-methylpyrrole-2-carbonyl}amino)-naphthalene-6-phosphonic acid;

carbonylbis-4-({4-[(4-aminopyrrole-1-methyl-2-carbonyl) amino]-1-methylpyrrole-2-carbonyl}amino)-naphthalene-2,5,6-triphosphonic acid;

carbonylbis-4-({4-[(4-aminopyrrole-1-methyl-2-carbonyl) amino]-1-methylpyrrole-2-carbonyl}amino)-naphthalene-1,5,7-triphosphonic acid;

carbonylbis-3-({4-[(4-aminopyrrole-1-methyl-2-carbonyl) amino]-1-methylpyrrole-2-carbonyl}amino)-naphthalene-1,5,7-triphosphonic acid;

carbonylbis-3-{[4-({4-[(4-aminopyrrole-1-methyl-2-carbonyl)amino]-1-methylpyrrole-2methylpyrrole-2-carbonyl]amino}naphthalene-1,5-diphosphonic acid;

carbonylbis-4-{[4-({4-[(4-aminopyrrole-1-methyl-2-carbonyl)amino]-1-methylpyrrole-2-carbonyl}amino)-1-methylpyrrole-2-carbonyl]amino}-naphthalene-1,7-diphosphonic acid;

carbonylbis-1-{[4-({4-[(4-aminopyrrole-1-methyl-2-carbonyl)amino]-1-methylpyrrole-2-carbonyl}amino)-1-methylpyrrole-2-carbonyl]amino}-naphthalene-5,7-diphosphonic acid;

carbonylbis-4-{[4-({4-[(4-aminopyrrole-1-methyl-2-carbonyl)amino]-1-methylpyrrole-2-carbonyl}amino)-1-methylpyrrole-2-carbonyl]amino}-naphthalene-5,7-diphosphonic acid; and carbonylbis-3-{[4-({4-[(4-aminopyrrole-1-methyl-2-carbonyl)amino]-1-methylpyrrole-2-carbonyl}amino)-1-methylpyrrole-2-carbonyl]amino}-naphthalene-1,5,7-triphosphonic acid;

and the $C_1$–$C_6$ alkyl and phenyl-$C_1$–$C_6$ alkyl esters and the pharmaceutically acceptable salts thereof.

Particularly preferred are the methyl, ethyl and benzyl esters and the sodium and potassium salts of said examples of specific compounds of the invention.

The compounds of formula (I) and the pharmaceutically acceptable salts thereof are hereafter also referred to as "the compounds of the invention" or as "the active agents of the invention".

The compounds of the invention, and the salts thereof can be prepared by a process comprising reacting a compound of formula (II)

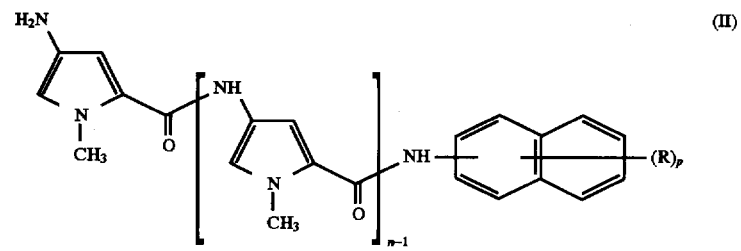

(II)

wherein n, p and R are as defined above, or a salt thereof, with a compound of formula (III)

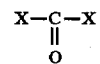

(III)

wherein each of the X groups, which may be the same or different, is a good leaving group, and, if desired, converting a compound of formula (I) into another compound of formula (I), and/or, if desired, salifying a compound of formula (I), thus obtained and/or, if desired, obtaining a free acid of formula (I) from an ester or a salt thereof; and/or, if desired, esterifying an acid of formula (I).

A salt of a compound of formula (II) may be a salt with organic or inorganic bases, for example those mentioned above as to the pharmaceutically acceptable salts of the invention, the sodium and potassium salts being the preferred.

Preferred examples of good leaving groups, according to the meaning of X, are halogen atoms, in particular chlorine, or other easily displaceable groups such as, imidazolyl, triazolyl, p-nitrophenoxy or trichloro-phenoxy.

The reaction of a compound of formula (II), or a salt thereof, with a compound of formula (III) is an analogy process and can be carried out according to well known methods; for example according to the conditions described in organic chemistry for this kind of reaction, i.e. for synthesis of urea derivatives. Preferably when in a compound of formula (III) X is a halogen atom, e.g. chlorine, the reaction may be carried out at a molar ratio of compound (II), or a salt thereof: compound (III) from about 1:0.5 to about 1:4.

According to a preferred embodiment of the invention, when the compound of formula (III) is phosgene, trichloromethylcarbonate or trichloromethylchloroformiate can be used as a phosgene source, according to known methods.

The reaction is preferably performed in an organic solvent, such as methylene chloride, dichloroethane, chloroform, toluene or dimethylsulphoxide, hexamethylphosphotriamide, dimethylacetamide or dimethylformamide, or their aqueous mixtures, or in water/dioxane, water/toluene or water/methylene chloride mixtures, in the presence of either an organic base such as triethylamine, diisopropylethylamine or pyridine or an inorganic base such as sodium bicarbonate or sodium acetate or a convenient buffer as known in the art. The reaction temperature may vary from about −10° C. to about 50° C. and the reaction time from about 1 to about 24 hours.

The compounds of formula (I) prepared according to the above described procedures may be purified by conventional methods such as by silica gel or alumina column chromatography, and/or by recrystallization from organic solvents such as lower aliphatic alcohols or dimethylformamide or their mixtures or in water containing mixtures.

Analogously, esterification or salification of an acid of formula (I) can be carried out by known methods in the art.

The compounds of formula (II), and the salts thereof, are new compounds and are a further object of the present invention.

The compounds of formula (II), and the salts thereof, can be obtained according to analogy processes.

For instance, a compound of formula (II) can be obtained by reduction of a compound of formula (IV) or a salt thereof (IV)

wherein
  n, p and R are as defined above by methods well known in the art.

The compounds of formula (IV) can be obtained by reacting an amine of formula (V), or a salt thereof (V)

wherein n and p are as defined above, with a compound of formula (VI)

(VI)

wherein n and X are as defined above.

Also the reaction of an amine of formula (V), or a salt thereof, with a compound of formula (VI) is a well known process.

Alternatively, a compound of formula (IV) wherein n is 2, 3 or 4 may be obtained by a multi-step-process comprising reacting a compound of formula (VII)

(VII)

wherein X is as defined above, with an amine of formula (V), or a salt thereof, as defined above. The reaction, which may be carried out according to known methods, provides a compound of formula (VIII) or a salt thereof (VIII)

wherein R and p are defined above.

A compound of formula (VIII), or a salt thereof, is reduced according to known methods to provide a compound of formula (IX), or a salt thereof (IX)

wherein p and R are as defined above, which in its turn is reacted with a compound of formula (VII), as defined above, thus obtaining a compound of formula (IV), as defined above, wherein n is 2. If a compound of formula (IV), wherein n is 3 or 4 is desired, further reduction and acylation steps are required.

The compounds of formula (VI) are known compounds or may be obtained, for example, according to Heterocycles, vol 27, No. 8, p. 1945–52 (1988).

The compounds of formula (VII) are known products or may be easily obtained according to known methods.

The amines of formula (V) as defined above and the salts thereof are new compounds and are a further object of this invention.

An amine of formula (V) or a salt thereof can be obtained by reducing a nitro derivative of formula (X) or a salt thereof (X)

wherein R and p are as defined above, according to known methods.

A nitro derivative of formula (X) can be obtained by nitration of a suitable free, esterified or salified mono-, di- or tri-phosphonic naphthalenic acid. In its turn said free, esterified or salified acid can be obtained by reacting a naphthalene compound substituted by 1, 2 or 3 trifluoromethanesulfonate group(s) or halogen atom(s), e.g. bromine or iodine, respectively, with a di-$C_1$–$C_6$ alkyl-, di-aryl-, e.g. di-phenyl- or di-aryl-alkyl, e.g. di-phenyl-$C_1$–$C_6$ alkyl phosphite, in presence of an organic basic agent, e.g. triethylamine, diisopropylamine or pyridine, and a suitable catalytic agent, e.g. tetrakis-triphenylphosphine palladium (O), platinum (O) or nickel (O), at a temperature ranging from about 0° C. to about 150° C.

A naphthalene compound substituted by 1, 2 or 3 trifluoromethanesulfonate groups can be obtained by reacting a mono-, di- or tri-hydroxy substituted naphthalene compound, respectively, with a reactive trifluoromethanesulfonic acid derivative, e.g. the chloride or anhydride, in the presence of an organic basic agent, e.g. pyridine or triethylamine, if the case in an organic inert solvent, e.g. methylene chloride, diethyl ether or toluene.

A salt of a compound of formula (IV), (V), (VIII), (IX) or (X) may be a salt with organic or inorganic bases, for example those mentioned above as to the compounds of formula (I), the sodium and potassium salts being the preferred ones.

PHARMACOLOGY

The new naphthalenephosphonic acids of formula (I), and the pharmaceutically acceptable salts thereof, according to the present invention, are angiogenesis inhibitors, as shown, e.g., by the fact that they have been found to be active in the chorioallantoic membrane test, according to the Folkman's method [Nature, 297, 307 (1982)]. Therefore the compounds of the present invention are useful in treating several pathological conditions in mammals, including humans, where the growth of new blood vessels is detrimental, for example, in chronic inflammation, diabetic retinopathy, psoriasis, rheumatoid arthritis and tumor growth. In particular, in the cancer therapy the compounds of the invention can be administered alone or in association with antitumor agents such as doxorubicin, 4'-iododoxorubicin, methoxy-morpholino-doxorubicin, etoposide, fluorouracil, melphalan, cyclophosphamide, bleomycin, vinblastin or mitomycin.

The compounds of the present invention have also been found to be endowed with TNF α-neutralizing activity and therefore they can be employed in humans for prophylactic and/or therapeutic use in any disease state in which TNFα is known to play a detrimental role. Typically such disease states are cachexia, septic shock, graft-versus-host disease, AIDS, cerebral malaria, rheumatoid arthritis. The TNF α-inhibiting activity of the compounds according to the present invention is proven, for instance, by the fact that they are active in inhibiting the cytotoxicity activity of human TNF α on untreated mouse LM cells. Accordingly, the new compounds of the invention can be used as angiogenesis inhibitors and/or as TNF α-neutralizing activity agents. The compounds of the invention can thus be used in the preparation of a medicament for use in the treatment of angiogenesis and/or for prophylactic and/or therapeutic use in a disease state in which TNF α plays a detrimental role. In these therapeutical applications the compounds of the invention can be administered by the usual routes, for example, parenterally, e.g. by intravenous injection or infusion, intramuscularly, subcutaneously, topically or orally. The dosage depends on the age, weight and conditions of the patient and on the administration route.

For example, a suitable dosage for administration to adult humans may range from about 0.5 to about 300 mg pro dose 1–4 times a day.

Moreover, the compounds of the present invention have been found to act directly as anti-lentivirus agents, in particular against Human Immunodeficiency Virus (HIV). For instance, the representative compounds of the invention carbonyl bis-3-({4-[(4-aminopyrrole-1-methyl-2-carbonyl) amino]-1-methylpyrrole-2-carbonyl}amino)-naphthalene-1, 5-diphosphonic acid; and carbonylbis-4-({4-[(4-aminopyrrole-1-methyl-2-carbonyl) amino]-1-methylpyrrole-2-carbonyl}amino)-naphthalene-1,7-diphosphonic acid have been found to be active in the biological test described in J. Natl. Cancer Inst. 8.1, 557–586 (1989).

A human patient suffering from lentivirus infection can thus be treated by a method comprising administering thereto an effective amount of one of the compounds of the invention. In this way, the compounds of the invention can be used to treat an infection attributable to a lentivirus, in particular a human immunodeficiency virus, especially HIV-1 or HIV-2.

The compounds of the invention can also be used in the preparation of a medicament for use in the treatment of a human patient suffering from lentivirus infection. The said medicament may be for use as an anti-lentivirus agent, for example an anti-HIV-1 or -HIV-2 agent. The said medicament may also be for use in ameliorating the symptoms of lentivirus-induced disease in a human patient suffering from lentivirus infection.

In particular the compounds of the invention can be used in the preparation of an agent to be used in the treatment of a human patient who is seropositive diseased, stressed or pathological as a result of infection with a lentivirus, in particular HIV, or who is suffering from induced disease, e.g., lymphadenopathy syndrome (LS), AIDS-related complex (ARC), AIDS or Kaposi's sarcoma. The condition of a human patient can thus be ameliorated or improved.

In these therapeutical applications the compounds of the invention can be administered by usual routes, for example, parenterally, e.g. by intravenous injection or infusion, intramuscularly, subcutaneously, topically or orally, intravenous injection or infusion being preferred. The dosage depends on the age, weight and condition of the patient and on the administration route. A suitable dosage for the compounds of the invention, for example carbonylbis-3-({4-[(4-aminopyrrole-1-methyl-2-carbonyl)amino]-1-methylpyrrole-2-carbonyl}amino)-naphthalene-1,5-diphosphonic acid or a pharmaceutically acceptable salt thereof, for administration to adult humans is from about 0.5 to about 300 mg per dose 1–4 times a day.

The compounds of the invention may be used in a method of treatment of the above mentioned pathological conditions comprising both separate and substantially contemporaneous administration of a composition containing a compound of formula (I), or a pharmaceutically acceptable salt thereof, and a pharmaceutical composition containing different pharmaceutically active agents. The present invention therefore further provides products comprising a compound of formula (I), or a pharmaceutically acceptable salt thereof, and a second active agent as a combined preparation for separate, simultaneous or sequential use in treating a human patient suffering from lentivirus infection, in particular infection with HIV. The second active agent is typically a drug that affects the pathogenesis of HIV-induced diseases.

For example, the compounds of the invention may be employed with various active agents, in particular those that affect reverse transcriptase, antimicrobial and antitumor agents or a mixture of two or more thereof. Drugs of interest include non-nucleoside reverse transcriptase inhibitors, e.g. nevirapine; nucleoside derivatives, e.g. zidovudine and didanosine; acyclovir; ribavirin; ascorbic acid; protease inhibitors; cytokine, e.g. IL-1, IL-2, IL-3 or IL-4; growth factors; interferons, e.g. alpha- or gamma-interferon; anti-tumor agents, e.g. doxorubicin, daunomycin, epirubicin, 4'-iododoxorubicin, methoxy-morpholino-doxorubicin, idarubicin, etoposide, fluorouracil, melphalan, cyclophosphamide, bleomycin, vinblastin and mitomycin; immunomodulating agents, in particular immunostimulants, gamma globulin, immune globulin and monoclonal antibody products, antibiotics and antimicrobial products. Typically, the antimicrobial agents may include a penicillin in conjunction with an aminoglycoside (e.g. gentamicin, tobramycin).

However several well known additional agents, e.g. cephalosporin, can be utilized.

The administration dosage of these drugs will vary, depending upon the disease status of the individual. The dosage regimen must therefore be tailored to the particular of the patient's conditions, response and associate treatments in a manner which is conventional for any therapy, and may need to be adjusted in response to changes in conditions and/or in light of other clinical conditions.

The pharmaceutical composition used in the invention may comprise a compound of formula (I) or a pharmaceutically acceptable salt thereof, as the active substance, in association with one or more pharmaceutically acceptable excipients and/or carriers. The pharmaceutical compositions are usually prepared following conventional methods and are administered in a pharmaceutically suitable form. For instance, solutions for intravenous injection or infusion may contain as carrier, for example, sterile water or, preferably, they may be in the form of sterile aqueous isotonic saline solutions. Suspensions or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride.

In the form for topical application, e.g. creams, lotions or pastes for use in dermatological treatment, the active ingredient may be mixed with conventional oleaginous or emulsifying excipients.

The solid oral forms, e.g. tablets and capsules, may contain, together with the active compound, diluents, e.g. lactose, dextrose, saccharose, cellulose, corn starch and potato starch; lubricants, e.g. silica, talc, stearic acid, magnesium or calcium stearate, and/or polyethylene glycols; binding agents, e.g. starches, arabic gum, gelatin, methylcellulose, carboxymethyl-cellulose, polyvinylpyrrolidone; disaggregating agents, e.g. a starch, alginic acid, alginates, sodium starch glycolate; effervescing mixtures; dyestuffs; sweeteners; wetting agents, for instance, lecithin, polysorbates, laurylsulphates; and, in general, non-toxic and pharmacologically inactive substances used in pharmaceutical formulations. Said pharmaceutical preparations may be manufactured in a known manner, for example by means of mixing, granulating, tabletting, sugar-coating, or filmcoating processes.

The following examples illustrate but do not limit the invention.

EXAMPLE 1

Carbonylbis-3-({4-[(4-aminopyrrole-1-methyl-2-carbonyl) amino]-1-methylpyrrole-2-carbonyl}amino)-naphthalene-1,5-diphosphonic acid octaethyl ester To an ice-cooled solution of tetraethyl 3-[1-methyl-2-pyrrolecarboxamido-4-(1-methyl-4-amino-2-pyrrolecarboxamido)]naphthalene-1,5-diphosphonate (4.23 g, 6.08 mmol as hydrochloride) and $Et_3N$ (3.5 ml, 25 mmol) in methylene chloride (ethanol free 100 ml) a solution of trichloro-methylcarbonate (325 mg, 1.09 mmol) in methylene chloride (10 ml) was added dropwise under stirring. After 3 hours at room temperature the whole was washed with $H_2O$, 1N Hcl, $NaHCO_3$ solution, dried and evaporated under reduced pressure.

The crude residue was purified by flash chromatography on silica gel 60 ($CH_2Cl_2$ 90—$CH_3OH$ 10).

The solid residue was taken up with ethyl acetate, filtered and dried to afford the title compound (3.11 g, m.p. 195°–205° C.) as microcrystalline pale brown solid.

200 Mhz $^1H$ NMR (DMSO-$d_6$): $\delta$10.45, 9.88 (two singlets, 2H); 9.23 (d, 1H, J=1.1 Hz); 8.7–8.5 (m, 2H); 8.17 (s, 1H); 8.12 (ddd, 1H, J=1.1 Hz, J=7.2 Hz, J=15.8 Hz); 7.63 (ddd, 1H, J=3.7 Hz, J=7.2 Hz, J=8.6 Hz); 7.35, 7.27 (two doublets, 2H, J=1.8 Hz); 7.03, 6.84 (two doublets, 2H, J=1.8 Hz); 4.2–3.9 (m, 8H); 3.84, 3.89 (two singlets, 6H); 1.3–1.1 (m, 12H). (–) FAB MS (M–H)$^-$=1344.

EXAMPLE 2

Carbonylbis-4-({4-[(4-aminopyrrole-1-methyl-2-carbonyl) amino]-1-methylpyrrole-2-carbonyl}amino)-naphthalene-1,7-diphosphonic acid octaethyl ester The method described in Example 1 with 780 mg of tetraethyl 4-[1-methyl-2-pyrrolecarboxamido-4-(1-methyl-4-amino-2-pyrrolecarboxamido)]-naphthalene-1,7-diphosphonate hydrochloride, as starting product, gave the title product as an orange solid (270 mg, 36%).

200 MHz $^1H$ NMR (DMSO-$d_6$): $\delta$9.91, 10.30 (two singlets, 2H); 8.94 (d, 1H, J=15.8 Hz); 8.0–8.3 (m, 3H); 7.7–8.0 (m, 2H); 7.32, 7.37 (two doublets, 2H, J=1.8 Hz); 6.84, 7.03 (two doublets, 2H, J=1.8 Hz); 3.9–4.2 (m, 8H); 3.85, 3.84 (two singlets, 6H); 1.1–1.3 (m, 12H). (–) FAB MS (M–H)$^-$=1344.

By analogous procedure the ethyl esters of the following compounds can be obtained:

carbonylbis-3-({4-[(4-aminopyrrole-1-methyl-2-carbonyl) amino]-1-methylpyrrole-2-carbonyl}amino)-naphthalene-1,6-diphosphonic acid;

carbonylbis-4-({4-[(4-aminopyrrole-1-methyl-2-carbonyl) amino]-1-methylpyrrole-2-carbonyl}amino)-naphthalene-1,6-diphosphonic acid;

carbonylbis-3-({4-[(4-aminopyrrole-1-methyl-2-carbonyl) amino]-1-methylpyrrole-2-carbonyl}amino)-naphthalene-5,7-diphosphonic acid;

carbonylbis-2-({4-[(4-aminopyrrole-1-methyl-2-carbonyl) amino]-1-methylpyrrole-2-carbonyl}amino)-naphthalene-1,5-diphosphonic acid;

carbonylbis-1-({4-[(4-aminopyrrole-1-methyl-2-carbonyl) amino]-1-methylpyrrole-2-carbonyl}amino)-naphthalene-5,7-diphosphonic acid;

carbonylbis-4-({4-[(4-aminopyrrole-1-methyl-2-carbonyl) amino]-1-methylpyrrole-2-carbonyl}amino)-naphthalene-5,7-diphosphonic acid;

carbonylbis-1-({4-[(4-aminopyrrole-1-methyl-2-carbonyl) amino]-1-methylpyrrole-2-carbonyl}amino)-naphthalene-5,6-diphosphonic acid;

carbonylbis-4-({4-[(4-aminopyrrole-1-methyl-2-carbonyl) amino]-1-methylpyrrole-2-carbonyl}amino)-naphthalene-5,6-diphosphonic acid;

carbonylbis-4-({4-[(4-aminopyrrole-1-methyl-2-carbonyl) amino]-1-methylpyrrole-2-carbonyl}amino)-naphthalene-2,5-diphosphonic acid;

carbonylbis-4-({4-[(4-aminopyrrole-1-methyl-2-carbonyl) amino]-1-methylpyrrole-2-carbonyl}amino)-naphthalene-6,7-diphosphonic acid;

carbonylbis-4-({4-[(4-aminopyrrole-1-methyl-2-carbonyl) amino]-1-methylpyrrole-2-carbonyl}amino)-naphthalene-2,6-diphosphonic acid;

carbonylbis-4-({4-[(4-aminopyrrole-1-methyl-2-carbonyl) amino]-1-methylpyrrole-2-carbonyl}amino)-naphthalene-2,7-diphosphonic acid;

carbonylbis-1-({4-[(4-aminopyrrole-1-methyl-2-carbonyl) amino]-1-methylpyrrole-2-carbonyl}amino)-naphthalene-5-phosphonic acid;

carbonylbis-4-({4-[(4-aminopyrrole-1-methyl-2-carbonyl) amino]-1-methylpyrrole-2-carbonyl}amino)-naphthalene-5-phosphonic acid;

carbonylbis-4-({4-[(4-aminopyrrole-1-methyl-2-carbonyl) amino]-1-methylpyrrole-2-carbonyl}amino)-naphthalene-6-phosphonic acid;

carbonylbis-1-({4-[(4-aminopyrrole-1-methyl-2-carbonyl) amino]-1-methylpyrrole-2-carbonyl}amino)-naphthalene-6-phosphonic acid;

carbonylbis-4-({4-[(4-aminopyrrole-1-methyl-2-carbonyl) amino]-1-methylpyrrole-2-carbonyl}amino)-naphthalene-2,5,6-triphosphonic acid;

carbonylbis-4-({4-[(4-aminopyrrole-1-methyl-2-carbonyl) amino]-1-methylpyrrole-2-carbonyl}amino)-naphthalene-1,5,7-triphosphonic acid; and carbonylbis-3-({4-[(4-aminopyrrole-1-methyl-2-carbonyl) amino]-1-methylpyrrole-2-carbonyl}amino)-naphthalene-1,5,7-triphosphonic acid.

EXAMPLE 3

Carbonylbis-3-({4-[(4-aminopyrrole-1-methyl-2-carbonyl) amino]-1-methylpyrrole-2-carbonyl}amino)-naphthalene-1, 5-diphosphonic acid and tetrasodium salt thereof.

To an ice-cooled solution of octaethyl ester of example 1 (1.00 g, 0.74 mmol) in dry $CH_3CN$ (100 ml) a solution of bromotrimethyl silane (10 ml) in $CH_3CN$ (10 ml) was added dropwise under stirring. After leaving 24 hours at room temperature, the organic volatiles were evaporated under reduced pressure. The residue was taken up with acetone and $H_2O$ (500 mg) diluted with $(CH_3)_2CO$ (10 ml) was added.

After stirring for 4 h, the separated microcrystalline solid was filtered, washed with acetone, methanol, ether and vacuum dried to give the title acid (779 mg).

Elemental analysis: $C_{45}H_{44}N_{10}O_{17}P_4$

Calc. %: C 48.22, H 3.96, N 12.50, O 24.27, P 11.05 Found %: C 44.46, H 4.26, N 11.18, P 9.48

200 MHz $^1$H NMR (DMSO-$d_6$, T=50° C.): δ9.74, 10.23 (two singlets, 2H); 9.07 (s, 1H); 8.72 (d, 1H, J=8.5 Hz); 8.47 (dd, 1H, J=1.9 Hz, J=16.9 Hz); 8.05 (dd, 1H, J=7.1 Hz, J=15.6 Hz); 8.01 (s, 1H); 7.48 (ddd, 1H, J=3.2 Hz, 5=7.1 Hz, J=8.5 Hz); 6.83, 7.00, 7.25, 7.31 (four doublets, 4H, J=1.8 Hz); 3.85, 3.89 (two singlets, 6H).

The acid thus obtained (650 mg, 0.58 mmol) was dissolved in $H_2O$ (50 ml) and neutralized with $NaHCO_3$ (195 mg, 2.32 mmol) to pH 6.5–7.

The solution was filtered, concentrated under reduced pressure to small volume and freeze-dried to microcrystalline pale brown salt.

Elemental analysis: $C_{45}H_{40}N_{10}Na_4O_{17}P_4$ (1208.70), found (calculated):

N 9.88 (11.59)%; loss on drying (100° C.) 12.75%.

200 MHz $^1$H NMR ($D_2O$+NaOD): δ8.76 (m, 2H); 8.02 (m, 2H); 7.47 (m, 1H); 6.61, 6.84, 6.99, 7.22 (four doublets, 4H, J=1.9 Hz); 3.76, 3.84 (two singlets, 6H).

EXAMPLE 4

Carbonylbis-4-({4-[(4-aminopyrrole-1-methyl-2-carbonyl) amino]-1-methylpyrrole-2-carbonyl}amino)-naphthalene-1, 7-diphosphonic acid and tetrasodium salt thereof.

The method described in Example 3 with 197 mg of carbonyl bis-4-({4-[(4-aminopyrrole-1-methyl-2-carbonyl) amino]-1-methylpyrrole-2-carbonyl}amino)-naphthalene-1, 7-diphosphonic acid octaethyl ester as starting product gave the title acid as an orange solid (160 mg, 98%).

200 MHz $^1$H NMR (DMSO-$d_6$, T=50° C.): δ6 9.78, 10.05 (two singlets, 2H); 9.13 (d, 1H, J=15.6 Hz); 8.0–8.2 (m, 3H); 7.6–7.9 (m, 2H); 6.85, 7.01, 7.29, 7.33 (four doublets, 4H, J=1.8 Hz); 3.85, 3.86 (two singlets, 6H).

Neutralization with $NaHCO_3$ gave the title tetrasodium salt as a pale brown solid (163 mg, 98%).

200 MHz $^1$H NMR ($D_2O$+NaOD, T=50° C.): δ9.04 (d, 1H, J=14 Hz); 8.03 (dd, 1H, J=7.4 Hz, J=13.7 Hz); 7.7–8.0 (m, 2H); 7.34 (dd, 1H, J=2.3 Hz, J=7.4 Hz); 6.78, 6.99 (two singlets, 2H); 3.80, 3.85 (two singlets, 6H).

Elemental analysis: $C_{45}H_{40}N_{10}Na_4O_{17}P_4$ calc. %: C 44.72, H 3.33, N 11.59 found %: C 34.33, H 3.50, N 8.58

By analogous procedure the following compounds can be obtained as free acids and sodium salts:

carbonylbis-3-({4-[(4-aminopyrrole-1-methyl-2-carbonyl) amino]-1-methylpyrrole-2-carbonyl}amino)-naphthalene-1,6-diphosphonic acid;

carbonylbis-4-({4-[(4-aminopyrrole-1-methyl-2-carbonyl) amino]-1-methylpyrrole-2-carbonyl}amino)-naphthalene-1,6-diphosphonic acid;

carbonylbis-3-({4-[(4-aminopyrrole-1-methyl-2-carbonyl) amino]-1-methylpyrrole-2-carbonyl}amino)-naphthalene-5,7-diphosphonic acid;

carbonylbis-2-({4-[(4-aminopyrrole-1-methyl-2-carbonyl) amino]-1-methylpyrrole-2-carbonyl}amino)-naphthalene-1,5-diphosphonic acid;

carbonylbis-1-({4-[(4-aminopyrrole-1-methyl-2-carbonyl) amino]-1-methylpyrrole-2-carbonyl}amino)-naphthalene-5,7-diphosphonic acid;

carbonylbis-4-({4-[(4-aminopyrrole-1-methyl-2-carbonyl) amino]-1-methylpyrrole-2-carbonyl}amino)-naphthalene-5,7-diphosphonic acid;

carbonylbis-1-({4-[(4-aminopyrrole-1-methyl-2-carbonyl) amino]-1-methylpyrrole-2-carbonyl}amino)-naphthalene-5,6-diphosphonic acid;

carbonylbis-4-({4-[(4-aminopyrrole-1-methyl-2-carbonyl) amino]-1-methylpyrrole-2-carbonyl}amino)-naphthalene-5,6-diphosphonic acid;

carbonylbis-4-({4-[(4-aminopyrrole-1-methyl-2-carbonyl) amino]-1-methylpyrrole-2-carbonyl}amino)-naphthalene-2,5-diphosphonic acid;

carbonylbis-4-({4-[(4-aminopyrrole-1-methyl-2-carbonyl) amino]-1-methylpyrrole-2-carbonyl}amino)-naphthalene-6,7-diphosphonic acid;

carbonylbis-4-({4-[(4-aminopyrrole-1-methyl-2-carbonyl) amino]-1-methylpyrrole-2-carbonyl}amino)-naphthalene-2,6-diphosphonic acid;

carbonylbis-4-({4-[(4-aminopyrrole-1-methyl-2-carbonyl) amino]-1-methylpyrrole-2-carbonyl}amino)-naphthalene-2,7-diphosphonic acid;

carbonylbis-1-({4-[(4-aminopyrrole-1-methyl-2-carbonyl) amino]-1-methylpyrrole-2-carbonyl}amino)-naphthalene-5-phosphonic acid;

carbonylbis-4-({4-[(4-aminopyrrole-1-methyl-2-carbonyl) amino]-1-methylpyrrole-2-carbonyl}amino)-naphthalene-5-phosphonic acid;

carbonylbis-4-({4-[(4-aminopyrrole-1-methyl-2-carbonyl) amino]-1-methylpyrrole-2-carbonyl}amino)-naphthalene-6-phosphonic acid;

carbonylbis-1-({4-[(4-aminopyrrole-1-methyl-2-carbonyl) amino]-1-methylpyrrole-2-carbonyl}amino)-naphthalene-6-phosphonic acid;

carbonylbis-4-({4-[(4-aminopyrrole-1-methyl-2-carbonyl) amino]-1-methylpyrrole-2-carbonyl}amino)-naphthalene-2,5,6-triphosphonic acid;

carbonylbis-4-({4-[(4-aminopyrrole-1-methyl-2-carbonyl) amino]-1-methylpyrrole-2-carbonyl}amino)-naphthalene-1,5,7-triphosphonic acid; and carbonylbis-3-({4-[(4-aminopyrrole-1-methyl-2-carbonyl) amino]-1-methylpyrrole-2-carbonyl}amino)-naphthalene-1,5,7-triphosphonic acid.

EXAMPLE 5

Tetraethyl3-[1-methyl-2-pyrrolecarboxamido-4-(1-methyl-4-amino-2-pyrrolecarboxamido)]naphthalene-1,5-diphosphonate hydrochloride Tetraethyl3-[1-methyl-2-pyrrolecarboxamido-4-(1-methyl-4-nitro-2-pyrrolecarboxamido)]naphthalene-1,5-diphosonate (4.50 g, 6.52 mmol) dissolved in methanol (350 ml) and aq. 1N HCl (7.0 ml) was hydrogenated with 5% Pd/c (500 mg) in a PARR apparatus until $H_2$ absorption ceased. After catalyst separation, methanol was evaporated under reduced pressure. The residue was taken up in diethyl ether and the separated microcrystalline solid was filtered, washed and dried at 60° C. under reduced pressure to give the title compound (4.43 g, 96%) as hydrochloride.

Elemental analysis: $C_{30}H_{40}ClN_5O_8P_2$ found (calc.) %: C 49.93 (51.76), H 5.93 (5.79), Cl 5.00 (5.09), N 9.61 (10.06) (-) FAB MS: $(M-H)^-=658$ 400 MHZ $^1$H NMR: δ10.13, 10.46 (two singlets, 2H); 9.85 (bs, 3H); 9.23 (s, 1H); 8.60 (d, 1H, J=8.5 Hz); 8.56 (dd, 1H, J=2.0 Hz, J=17.3 Hz); 8.12 (dd, 1H, J=7.3 Hz, J=17.0 Hz); 7.64 (ddd, 1H, J=3.5 Hz, J=7.3 Hz, J=8.5 Hz); 7.26, 7.36 (two doublets, 2H, J=1.8 Hz); 7.00, 7.10 (two doublets, 2H, J=2.0 Hz); 4.00–4.2 (m, 8H); 3.89 (s, 6H); 1.2–1.3 (m, 12H).

EXAMPLE 6

Tetraethyl 4-[1-methyl-2-pyrrolecarboxamido-4-(1-methyl-4-amino-2-pyrrolecarboxamido)]-naphthalene-1,7-diphosphonate hydrochloride.

The method described in example 5 with 1.0 g of tetraethyl4-[1-methyl-2-pyrrolecarboxamido-4-(1-methyl-4-nitro-2-pyrrolecarboxamido)]-naphthalene-1,7-diphosphonate as starting material gave the title product as a brown solid (0.95 g, 94%).

80 MHz $^1$H NMR (DMSO-$d_6$): δ10.3 (s, 1H); 10.15 (s, 1H); 10.1 (br, 3H); 8.95 (d, 1H); 7.65–8.4 (m, 4H); 7.3–7.4 (m, 2H); 7.0–7.15 (m, 2H); 3.9–4.3 (m, 8H); 3.9 (s, 3H); 3.85 (s, 3H); 1.1–1.4 (m, 12H).

EXAMPLE 7

Tetraethyl3-[1-methyl-2-pyrrolecarboxamido-4-(1-methyl-4-nitro-2-pyrrolecarboxamido)]naphthalene-1,5-diphosphonate.

Tetraethyl 3-(1-methyl-4-amino-2-pyrrolecarboxamido) naphthalene-1,5-diphosphonate (7.3 mmol) as hydrochloride and triethylamine (3.5 ml, 25 mmol) in $CH_2Cl_2$ (ethanol free, 100 ml) were treated dropwise, with ice-bath cooling, with 1-methyl-4-nitro-2-pyrrolecarboxylic acid chloride (1.41 g, 7.5 mmol) in 15 ml $CH_2Cl_2$. After leaving 1 h in ice and 1 h at room temperature, the organic phase was washed with acid and $NaHCO_3$ solution, dried ($Na_2SO_4$) and evaporated under reduced pressure. Crude residue redissolved in ethanol (20 ml) was scratched to induce crystal formation; crystallization was completed with diethyl ether (20 ml) and the separated crystalline yellow solid was filtered, washed with an ethanol-diethyl ether 1:1 mixture and dried at 50° under reduced pressure to yield the title compound (4.50 g, m.p. 163°–168° C., 89%).

Elemental analysis: $C_{30}H_{37}N_5O_{10}P_2$ found (calc.) %: N 9.85 (10.16) (-) FAB MS $(M-H)^-=688$.

400 MHz $^1$H NMR (DMSO-$d_6$): δ10.34, 10.49 (two singlets, 2H); 9.23 (s, 1H); 8.61 (d, 1H, J=8.4 Hz); 8.57 (dd, 1H, J=2.0 Hz, J=17.6 Hz); 8.12 (dd, 1H, J=7.0 Hz, J=16.1 Hz); 7.63 (ddd, 1H, J=4.2 Hz, J=7.0 Hz, J=8.4 Hz); 7.60, 8.19 (two doublets, 2H, J=1.8 Hz); 7.26, 7.37 (two doublets, 2H, J=1.8 Hz); 4.0–4.2 (m, 8H); 3.90, 3.96 (two singlets, 6H); 1.1–1.3 (m, 12H).

EXAMPLE 8

Tetraethyl 4-[1-methyl-2-pyrrolecarboxamido-4-(1-methyl-4-nitro-2-pyrrolecarboxamido)]-naphthalene-1,7-diphosphonate.

The method described in the example 7 with 1.84 g of tetraethyl 4-(1-methyl-4-amino-2-pyrrolecarboxamido) naphthalene-1,7-diphosphonate hydrochloride as starting material gave 1.89 g of the title product (85%).

200 MHZ $^1$H NMR (DMSO-$d_6$): δ10.34, 10.37 (two singlets, 2H); 8.94 (d, 1H, J=16.0 Hz); 8.1–8.3 (m, 2H); 7.7–7.9 (m, 9H); 7.62, 8.20 (two doublets, 2H, J=2.1 Hz); 7.32, 7.40 (two doublets, 2H, J=1.9 Hz); 3.9–4.2 (m, 8H); 3.86, 3.97 (two singlets, 6H); 1.1–1.3 (m, 12H). (-) FAB MS $(M-H)^-=688$.

EXAMPLE 9

Tetraethyl 3-(1-methyl-4-amino-2-pyrrolecarboxamido) naphthalene-1,5-diphosphonate Tetraethyl 3-(1-methyl-4-nitro-2-pyrrolecarboxamido) naphthalene-1,5-diphosphonate (4.15 g, 7.31 mmol) dissolved in methanol (150 ml) and 1N HCl (7.5 ml) was hydrogenated in presence of 5% Pd/C in a PARR apparatus until $H_2$ absorption ceased. After catalyst filtration on filter aid, the methanol was evaporated under reduced pressure and the residue was dried in vacuum and passed to the acylation without further purification.

80 MHz $^1$H NMR (CDCl$_3$): δ9.6 (s, 1H); 9.05 (m, 1H); 8.67 (dd, 1H, J=1.9 Hz, J=17.6 Hz); 8.67 (d, 1H, J=8.6 Hz); 8.12 (dd, 1H, J=6.5 Hz, J=15.9 Hz); 7.75 (s, 1H); 7.55 (m, 1H); 6.87 (s, 1H); 3.9–4.4 (m, 8H); 3.75 (s, 3H); 1.0–1.4 (m, 12H).

EXAMPLE 10

Tetraethyl 4-(1-methyl-4-amino-2-pyrrolecarboxamido) naphthalene-1,7-diphosphonate hydrochloride The method described in the example 9 with 1.89 g of tetraethyl 4-(1-methyl-4-nitro-2-pyrrolecarboxamido) naphthalene-1,7-diphosphonate as starting material gave 1.84 g of the title product as a brown solid (96%).

80 MHz $^1$H NMR (DMSO-$d_6$): δ10.45 (s, 1H); 10.2 (br, 3H); 8.95 (d, 1H), 7.65–8.4 (m, 4H); 7.2–7.35 (m, 2H); 3.8–4.4 (m, 11H); 1.1–1.4 (m, 12H).

EXAMPLE 11

Tetraethyl 3-(1-methyl-4-nitro-2-pyrrolecarboxamido) naphthalene-1,5-diphosphonate To an ice-cooled solution of tetraethyl 3-amino-naphthalene-1,5-diphosphonate hydrochloride hemihydrate (3.75 mg, 8.14 mmol) and triethylamine (3.75 ml, 27 mmol) in $CH_2Cl_2$ (ethanol free, 60 ml) was added dropwise 1-methyl-4-nitro-2-pyrrolecarboxylic acid chloride (1.89 g, 10 mmol) in 15 ml $CH_2Cl_2$.

After leaving for 4 hours at room temperature, the organic phase was washed with $H_2O$, 1N HCl followed by 5% $NaHCO_3$, dried ($Na_2SO_4$) and evaporated under reduced pressure to small volume and then purified by flash chromatography on silica gel 60 ($CH_2Cl_2$ 95-$CH_3OH$ 5).

The solid residue was taken up with diethyl ether, filtered and dried, to afford the title compound (4.17 g, m.p. 250.5°–252.5° C., 90%).

Elemental analysis: $C_{24}H_{31}N_3O_9P_2$ found (calc.) %: C 50.87 (50.79), H 5.53 (5.51), N 7.35 (7.40).

80 MHz $^1H$ NMR ($CDCl_3$): δ9.77 (s, 1H); 9.23 (d, 1H, J=2.2 Hz); 8.65 (dd, 1H, J=1.4 Hz, J=8.4 Hz); 8.55 (dd, 1H, J=2.2 Hz, J=17.4 Hz); 8.13 (ddd, 1H, J=1.4 Hz, J=7.3 Hz, J=16.0 Hz); 7.3–7.7 (m, 3H); 3.9–4.5 (m, 8H); 3.87 (s, 3H); 1.1–1.6 (m, 12H). EI MS $(M)^+$=567.

EXAMPLE 12

Tetraethyl 4-(1-methyl-4-nitro-2-pyrrolecarboxamido)naphthalene-1,7-diphosphonate The method described in the example 11 with 2.0 g of tetraethyl 1,7-diphosphonate-4-aminonaphthalene hydrochloride, as starting compound, gave 2.63 g of crude title product that was recrystallized from benzene, affording 1.90 g of microcrystalline white solid (m.p. 204°–205° C., 76%).

200 MHz $^1H$ NMR ($CDCl_3$): δ9.89 (s, 1H); 8.85 (dd, 1H, J=1.5 Hz, J=15.9 Hz); 7.9–8.1 (m, 2H); 7.79 (dd, 1H, J=3.4 Hz, J=7.9 Hz); 7.67, 8.05 (two doublets, 2H, J=1.8 Hz); 7.52 (ddd, 1H, J=1.5 Hz, J=8.7 Hz, J=11.6 Hz); 4.0–4.3 (m, 8H); 4.04 (s, 3H); 1.2–1.4 (m, 12H). EI MS $(M)^+$=567.

EXAMPLE 13

Tetraethyl3-aminonaphthalene-1,5-diphosphonate

Tetraethyl3-nitronaphthalene-1,5-diphosphonate (4.00 g, 9.0 mmol) dissolved in methanol (150 ml) and 1N HCl aqueous solution (10 ml) was stirred with $H_2$ and 5% Pd/C in PARR apparatus until $H_2$ absorption ceased. After catalyst filtration on filter aid, the methanol was evaporated under reduced pressure; the residue was stirred with ethanol (10 ml) and diethyl ether (50 ml) and the separated crystalline solid was filtered, washed and dried to yield the title product isolated as the hydrochloride hemihydrate (3.78 g, decomp. 230°–240° C., 91%).

Elemental analysis: $C_{18}H_{28}ClNO_6P_2 \cdot 0.5H_2O$ found (calc.) %:

C 46.99 (46.91); H 6.32 (6.34); N 3.02 (3.04).

80 MHz $^1H$ NMR ($CDCl_3$): δ8.3 (bs, 3H); 9.03 (d, 1H, J=2.1 Hz); 8.77 (d, 1H, J=8.5 Hz); 8.50 (dd, 1H, J=2.1 Hz, J=16.6 Hz); 8.26 (ddd, 1H, J=1.3 Hz, J=7.2 Hz, J=15.6 HZ); 7.65 (ddd, 1H, J=3.9 Hz, J=7.2 Hz, J=8.5 Hz); 3.9–4.5 (m, 8H); 1.3–1.5 (m, 12H).

EXAMPLE 14

Tetraethyl 1,7-diphosphonate-4-aminonaphthalene hydrochloride.

The method described in the example 13 with 2.7 g of tetraethyl 1,7-diphosphonate-4-nitronaphthalene gave 2.6 g of the title product as a pale yellow solid (94%).

80 MHz $^1H$ NMR ($CDCl_3$+$D_2O$): δ8.9 (d, 1H); 8.1 (dd, 1H); 7.65–7.95 (m, 2H); 6.85 (dd, 1H); 3.9–4.4 (m, 8H); 1.2–1.5 (m, 12H).

EXAMPLE 15

Tetraethyl 3-nitronaphthalene-1,5-diphosphonate.

Tetraethyl naphthalene-1,5-diphosphonate (10.21 g, 25.5 mmol) was dissolved portionwise in ice-cooled 96% $H_2SO_4$ and sulphonitric mixture (2.5 ml 90% $HNO_3$ in 7.5 ml 96% $H_2SO_4$) was added dropwise in 15 min.

After 30 min in ice-cooling, the reaction mixture was poured into ice-$H_2O$ mixture and extracted with ethyl acetate. The organic extract was washed with $H_2O$, $NaHCO_3$ solution, dried, concentrated under reduced pressure to 20 ml and diluted with 30 ml cyclohexane. After ice-cooling, the separated crystalline solid was filtered, washed and dried to yield the title compound (8.48 g, m.p. 117°–118.5° C., 74.7%).

Elemental analysis: $C_{18}H_{25}NO_8P_2$ found (calc.) %:

C 48.31 (48.54), H 5.64 (5.66), N 2.98 (3.14):

80 MHz $^1H$ NMR ($CDCl_3$): δ9.75 (dd, 1H, J=2.3 Hz, J=1.0 Hz); 8.97 (dd, 1H, J=2.3 Hz, J=16.6 Hz); 8.93 (m, 1H); 8.46 (ddd, 1H, J=1.3 Hz, J=7.1 Hz, J=15.9 Hz); 7.85 (ddd, 1H, J=3.6 Hz, J=7.1 Hz, J=8.4 Hz); 3.9–4.6 (m, 8H); 1.38 (t, 12H, J=7.2 Hz); EI MS $(M)^+$=445.

EXAMPLE 16

Tetraethyl 1,7-diphosphonate-4-nitronaphthalene.

1,7-ditrifluoromethanesulfonate-4-nitronaphthalene (266 mg, 0.57 mmol), diethylphosphite (315 mg, 2.28 mmol) and triethylamine (345 mg, 3.42 mmol) were dissolved in 20 ml of $CH_3CN$ under $N_2$.

Tetrakis(triphenylphosphine)palladium (0) (50 mg, 0.043 mmol) was added in one portion and the resulting mixture was refluxed for 2 hours.

After cooling, the solvent was removed under reduced pressure and the residue was redissolved in ethyl acetate, washed with $H_2O$, diluted hydrochloric acid, $NaHCO_3$ solution, $H_2O$, dried and evaporated under vacuum. Purification with column chromatography ($SiO_2$, ethyl acetate/methanol 96/4 as eluent) afforded the title product as a yellow solid (198 mg, m.p. 54°–57° C., 78%).

80 MHz $^1H$ NMR ($CDCl_3$): δ9.15 (dd, 1H); 7.9–8.6 (m, 4H); 4.0–4.5 (m, 8H); 1.1–1.5 (m, 12H).

EXAMPLE 17

Tetraethyl naphthalene-1,5-diphosphonate

Naphthalene-1,5-ditrifluoromethanesulfonate (16.46 g, 40 mmol) (prepared treating 1,5-dihydroxynaphthalene with trifluoromethanesulfonic anhydride in pyridine, m.p. 112°–113° C.), diethyl phosphite (13.81 g 100 mmol), dry N,N-diisopropylethylamine (15.51 g, 120 mmol), tetrakis(triphenylphosphine) palladium (0) (1.00 g, 0.86 mmol) in 50 ml dry N,N-dimethylformamide were heated at 95°–100° C. for 3 hours. After cooling, the reaction mixture was poured into $H_2O$ and extracted with ethyl acetate. The organic extract was washed with $H_2O$, diluted acid, $NaHCO_3$ solution, $H_2O$, dried ($Na_2SO_4$), concentrated under reduced pressure to 50 ml and diluted with 25 ml diethyl ether. After ice-cooling, the separated crystalline solid was filtered, washed with diethyl ether and dried to yield the title product (12.23 g, m.p. 169°–171° C., 76.4%).

Elemental analysis: $C_{18}H_{26}O_6P_2$ found (calc.) %: C 53.74 (54.00), H 6.53 (6.55). EI MS $(M)^+$=400.

80 MHz $^1H$ NMR ($CDCl_3$): δ8.82 (dd, 2H, J=8.7 Hz, J=1.2 Hz); 8.30 (ddd, 2H, J=1.2 Hz, J=6.9 Hz, J=15.6 Hz); 7.65 (ddd, 2H, J=3.9 Hz, J=6.9 Hz, J=8.7 Hz); 3.9–4.5 (m, 8H); 1.32 (t, 12H, J=7.2 Hz).

EXAMPLE 18

1,7-ditrifluoromethanesulfonate-4-nitronaphthalene

Naphthalene-1,7-ditrifluoromethanesulfonate (2.12 g, 5 mmol) (prepared treating 1,7-dihydroxynaphthalene with trifluoromethanesulfonic anhydride in pyridine) was added in small portions to 90% nitric acid (12.5 ml) cooled at −10° C. (ice-salt bath).

The resulting reaction mixture was stirred for 30 min, then poured into 100 g of ice/water and extracted with diethyl ether.

The organic extract was washed with $H_2O$, $NaHCO_3$ solution, $H_2O$ and dried.

The solvent was removed under reduced pressure and the residue purified by flash chromatography ($SiO_2$). Elution with cyclohexane/ethyl acetate 90/10 afforded the title product as a pale yellow crystalline solid (1.96 g, 83%).

80 MHz $^1$H NMR ($CDCl_3$): δ8.8 (d, 1H, J=9.6 Hz); 8.3 (d, 1H, J=8.8 Hz); 8.1 (d, 1H, J=2.8 Hz); 7.65–7.85 (m, 2H).

EXAMPLE 19

Carbonylbis-3-({4-[(4-aminopyrrole-1-methyl-2-carbonyl)amino]-1-methylpyrrole-2-carbonyl}amino)-1-methylpyrrole-2-carbonyl]amino}naphthalene-1,5-diphosphonic acid octaethyl ester.

Tetraethyl3-[1-methyl-2-pyrrolecarboxamido-4-(1-methyl-4-amino-2-pyrrolecarboxamido)]naphthalene-1,5-diphosphonate as hydrochloride (920 mg, 1.32 mmol) dissolved in dimethylformamide and 4,4'-carbonylbis-[2-(N-imidazolecarbonyl)-4-amino-1-methylpyrrole](250 mg, 0.62 mmol) was heated in 3 hours at 50°–70° until complete dissolution of imidazole derivative. Dimethylformamide was evaporated under reduced pressure; the residue was dissolved in $CH_2Cl_2$ and washed with $H_2O$, 0.5 N HCl, 5% $NaHCO_3$ solution, saturated NaCl solution, dried $Na_2SO_4$ and evaporated under reduced pressure.

The crude residue was purified by flash chromatography on silica gel, eluting with $CH_2Cl_2$/EtOH 85/15, affording the title compound as a pale brown crystalline solid (710 mg, 68% yield).

200 MHz $^1$H NMR (DMSO-$d_6$): δ10.46, 10.00, 9.83 (three singlets, 3H); 9.24 (s, 1H); 8.7–8.5 (m, 2H); 8.21 (s, 1H); 8.12 (ddd, 1H, J=1.2 Hz, J=7.1 Hz, J=16.8 Hz); 7.64 (ddd, 1H, J=3.7 Hz, J=7.1 Hz, J=8.7 Hz); 7.35, 7.28, 7.24, 7.08, 7.02, 6.81 (six doublets, 6H, J=1.7 Hz); 4.3–4.0 (m, 8H); 3.89, 3.86, 3.83 (three singlets, 9H); 1.4–1.2 (m, 12H). (−)FAB MS (M−H)$^-$=1587.

EXAMPLE 20

Carbonylbis-4-{[4-({4-[(4-amino-1-methylpyrrole-2-carbonyl)amino]-1-methylpyrrole-2-carbonyl}amino)-1-methylpyrrole-2-carbonyl]amino}-naphthalene-1,7-diphosphonic acid octaethyl ester The compound tetraethyl4-[1-methyl-2-pyrrolecarboxamido-4-(1-methyl-4-amino-2-pyrrolecarboxamido)]naphthalene-1,7-diphosphonate hydrochloride (172 mg, 2.48 mmol), and 4,4'-carbonylbis-[2-(N-imidazolecarbonyl)-4-amino-1-methylpyrrole] (503 mg, 1.24 mmol) were suspended into dry dimethylformamide (30 ml) and the whole was stirred at 70° C. for 2.5 hours. The solvent was evaporated under reduced pressure and the residue was chromatographed on a silica gel column with methylene chloride/ethanol 4/1 as eluent, affording the title product as a pale yellow solid (600 mg).

80-MHz $^1$H NMR (DMSO-$d_6$): δ1.25 (m, 12H, 4-$CH_2CH_3$); 3.7–4.3 (m, 17H, 4-$CH_2CH_3$+3-$CH_3$); 6.8, 7.0, 7.1, 7.2 (four doublets, 4H, pyrroles); 7.35 (s, 2H, pyrroles); 7.6–8.4 (m, 5H, 2+3+5+6+NHCO ureic); 8.95 (d, 1H, 8); 9.8, 10.0, 10.25 (three singlets, 3H, 3-CONH). (−) FAB MS (M−H)$^-$=1588.

By analogous procedure the following compounds can be obtained as free-acids and sodium salts:

Carbonylbis-1-{[4-({4-[(4-aminopyrrole-1-methyl-2-carbonyl)amino]-1-methylpyrrole-2-carbonyl}amino)-1-methylpyrrole-2-carbonyl]amino}-naphthalene-5,7-diphosphonic acid;

Carbonylbis-4-{[4-({4-[(4-aminopyrrole-1-methyl-2-carbonyl)amino]-1-methylpyrrole-2-carbonyl}amino)-1-methylpyrrole-2-carbonyl]amino}-naphthalene-5,7-diphosphonic acid; and Carbonylbis-3-{[4-({4-[(4-aminopyrrole-1-methyl-2-carbonyl)amino]-1-methylpyrrole-2-carbonyl}amino)-1-methylpyrrole-2-carbonyl]amino}-naphthalene-1,5,7-triphosphonic acid.

EXAMPLE 21

Carbonylbis-3-{[4-({4-[(4-aminopyrrole-1-methyl-2-carbonyl)amino]-1-methylpyrrole-2-carbonyl}amino)-1-methylpyrrole-2-carbonyl]amino}naphthalene-1,5-diphosphonic acid and tetrasodium salt.

The octaethyl ester compound obtained in Example 19 (620 mg, 0.39 mmol) in $CH_2Cl_2$ (50 ml, ethanol free) was treated with bromotrimethylsilane (3.9 ml, 30 mmol) as described in Example 3. After work up, the title acid was obtained as a pale brown crystalline saline (540 mg).

200-MHz $^1$H NMR (DMSO-$d_6$): δ10.32, 9.98, 9.83 (three singlets, 3H); 9.08 (s, 1H); 8.68 (d, 1H, J=8.9 Hz); 8.48 (dd, 1H, J=2.2 Hz, J=17.1 Hz); 8.1 (bs, 1H); 8.04 (ddd, 1H, J=1.3 Hz, J=7.1 Hz, J=15.8 Hz); 7.50, 7.26, 7.24, 7.06, 7.01, 6.81 (six doublets, 6H, J=1.7 Hz); 3.88, 3.86, 3.83 (three singlets, 9H). (−) FAB MS (M−H)$^-$=1363.

The acid thus obtained (520 mg) was dissolved in $H_2O$ (50 ml) and neutralized with 0.5N NaOH to pH 6.0. The solution was filtered, concentrated to small volume under reduced pressure and freeze-dried to microcrystalline pale brown salt.

Elemental analysis: $C_{57}H_{52}N_{14}Na_4O_{19}P_4$ (1452.95), found (calc.) %:

C 39.08 (47.11); H 5.11 (3.61); N 11.08 (13.50); loss on drying 16.00.

400-MHz $^1$H NMR (DMSO-$d_6$): same as the free acid. (−) FAB MS (M−H)$^-$=1451, (M−Na)$^-$=1429.

EXAMPLE 22

Carbonylbis-4-{[4-({4-[(4-aminopyrrole-1-methylpyrrole-2-carbonyl)amino]-1-methyl-pyrrole-2-carbonyl}amino)-1-methyl-2-carbonyl]amino}-naphthalene-1,7-diphosphonic acid and the tetrasodium salt.

The compound carbonylbis-4-{[4-({4-[(4-amino-1-methyl pyrrole-2-carbonyl)amino]-1-methylpyrrole-2-carbonyl}amino)-1-methylpyrrole-2-carbonyl]amino}-naphthalene-1,7-diphosphonic acid octaethyl ester (578 mg, 0.364 mmol), was dissolved into dry methylene chloride (75 ml) and, under stirring, under nitrogen, at 0° C., bromotrimethylsilane (4.54 ml, 35 mmol) was added dropwise. The whole was stirred at 0° C. for 1 hour then at room temperature for 66 hours. The solvent was evaporated, the residue was suspended into acetone (100 ml) and treated with water/acetone 1/5 (6 ml). The whole was stirred at room temperature for 3 hours and filtered affording the title product as free acid (490 mg, brown solid). 80-MHz $^1$H NMR (DMSO-$d_6$): δ3.7–4.0 (m, 9H, 3-CH$_3$); 6.8, 7.0, 7.1, 7.2 (four doublets, 4H, pyrroles); 7.35 (m, 2H, pyrroles); 7.6–8.3 (m, 5H, 2+3+5+6+NHCO ureic); 9.1 (d, 1H, 8); 9.8, 10.0, 10.15 (three singlets, 3H, 3-CONH). (–) FAB MS (M–H)$^-$=1363.

The acid thus obtained (480 mg, 0.352 mmol) was dissolved into water (20 ml) and neutralized with sodium hydrogencarbonate (118 mg, 1.406 mmol). The tetrasodium salt solution was filtered and freeze dried affording the title compound as a soft beige solid (515 mg).

400-MHz $^1$H NMR (DMSO-$d_6$+CF$_3$COOH): δ3.84, 3.86, 3.87 (three singlets, 9H, 3-NCH$_3$); 6.81, 7.03, 7.10, 7.24, 7.32, 7.37 (six doublets, J=1.7 Hz, 6H, pyrroles); 7.72 (dd, J=2.4 Hz, J=7.9 Hz, 1H, 3); 7.77 (m, 1H, 6); 8.10 (m, 2H, 5+2); 8.3 (bs, 1H, NHCO ureic); 9.10 (d, J=15.4, 1H, 8); 9.85, 10.02, 10.19 (three singlets, 3H, 3-CONH). (–) FAB MS (M+H–2Na)$^-$=1407.

By analogous procedure the following compounds can be obtained as free-acids and sodium salts:

carbonylbis-1-{[4-({4-[(4-aminopyrrole-1-methyl-2-carbonyl)amino]-1-methylpyrrole-2-carbonyl}amino)-1-methylpyrrole-2-carbonyl]amino}-naphthalene-5,7-diphosphonic acid;

carbonylbis-4-{[4-({4-[(4-aminopyrrole-1-methyl-2-carbonyl)amino]-1-methylpyrrole-2-methylpyrrole-2-carbonyl]amino}-naphthalene-5,7-diphosphonic acid; and carbonylbis-3-{[4-({4-[(4-aminopyrrole-1-methyl-2-carbonyl)amino]-1-methylpyrrole-2-carbonyl}amino)-1-methylpyrrole-2-carbonyl]amino}-naphthalene-1,5,7-triphosphonic acid.

EXAMPLE 23

4–4'-carbonylbis-4-amino-1-methylpyrrole-2-carboxylic acid and 4–4'-carbonylbis-[2-(N-imidazolecarbonyl)-4-amino-1-methylpyrazole]

To a solution of 4-amino-1-methylpyrrole-2-carboxylic acid (4.00 g, 22.6 mmol as hydrochloride), sodium bicarbonate (7.56 g, 90 mmol) in water (75 ml) and 1,4-dioxane (25 ml) a solution of bis-(trichloromethyl) carbonate (1.25 g, 4.2 mmol) dissolved in 1,4-dioxane (10 ml) was added dropwise, with stirring and ice-cooling. The reaction mixture was acidified to pH 1–2 with diluted hydrochloric acid, the precipitated white solid filtered, washed with H$_2$O and dried to give the title acid (3.89 g, 95% yield).

$^1$H NMR (DMSO-$d_6$): δ12.1 (b, 1H, exch. with D$_2$O); 8.2 (s, 1H, exch. with D$_2$O); 7.12 (d, 1H); 6.62 (d, 1H); 3.80 (s, 3H).

To a solution of the above acid (3.29 g, 10.75 mmol) in dimethylformamide (50 ml) N,N'-carbonyldiimidazole (5.80 g, 32.6 mmol) was added portionwise, with stirring, at room temperature. After 4 hours the precipitated solid was filtered, washed with dimethylformamide, Et$_2$O and dried to give the title compound (3.90 g, 90% yield).

$^1$H NMR (DMSO-$d_6$): δ8.75 (bs, 1H); 8.25 (m, 1H); 7.70 (t, 1H); 7.52 (d, 1H); 7.13 (m, 1H); 6.80 (d, 1H); 3.90 (s, 3H).

EXAMPLE 24

Intramuscular injection 40 mg/ml.

An injectable pharmaceutical preparation can be manufactured by dissolving 40 g of carbonylbis-3-({4-[(4-aminopyrrole-1-methyl-2-carbonyl)amino]-1-methyl-pyrrole-2-carbonyl}amino)-naphthalene-1,5-diphosphonic acid tetrasodium salt in water for injection (1000 ml) and sealing ampoules of 1–10 ml.

We claim:

1. A compound of formula (I)

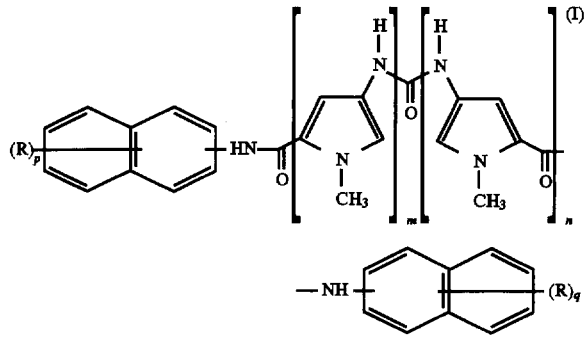

wherein each of m and n, which are the same, is an integer of 1 to 4; each of p and q, which are the same, is an integer of 1 to 3; and each of the R groups, which are the same, is a free phosphonic acid group, a pharmaceutically acceptable salt thereof, or a C$_1$–C$_6$ alkyl or phenyl-C$_1$–C$_6$ alkyl ester thereof.

2. A compound of formula (I), as defined in claim 1, wherein each of m and n is 2 and each of p and q is 2.

3. A compound selected from the group consisting of carbonylbis-3-({4-[(4-aminopyrrole-1-methyl-2-carbonyl)amino]-1-methylpyrrole-2-carbonyl}amino)-naphthalene-1,5-diphosphonic acid;

carbonylbis-4-({4-[(4-aminopyrrole-1-methyl-2-carbonyl)amino]-1-methylpyrrole-2-carbonyl}amino)-naphthalene-1,7-diphosphonic acid;

carbonylbis-3-({4-[(4-aminopyrrole-1-methyl-2-carbonyl)amino]-1-methylpyrrole-2-carbonyl}amino)-naphthalene-1,6-diphosphonic acid;

carbonylbis-4-({4-[(4-aminopyrrole-1-methyl-2-carbonyl)amino]-1-methylpyrrole-2-carbonyl}amino)-naphthalene-1,6-diphosphonic acid;

carbonylbis-3-({4-[(4-aminopyrrole-1-methyl-2-carbonyl)amino]-1-methylpyrrole-2-carbonyl}amino)-naphthalene-5,7-diphosphonic acid;

carbonylbis-2-({4-[(4-aminopyrrole-1-methyl-2-carbonyl)amino]-1-methylpyrrole-2-carbonyl}amino)-naphthalene-1,5-diphosphonic acid;

carbonylbis-1-({4-[(4-aminopyrrole-1-methyl-2-carbonyl)amino]-1-methylpyrrole-2-carbonyl}amino)-naphthalene-5,7-diphosphonic acid;

carbonylbis-4-({4-[(4-aminopyrrole-1-methyl-2-carbonyl)amino]-1-methylpyrrole-2-carbonyl}amino)-naphthalene-5,7-diphosphonic acid;

carbonylbis-1-({4-[(4-aminopyrrole-1-methyl-2-carbonyl)amino]-1-methylpyrrole-2-carbonyl}amino)-naphthalene-5,6-diphosphonic acid;

carbonylbis-4-({4-[(4-aminopyrrole-1-methyl-2-carbonyl)amino]-1-methylpyrrole-2-carbonyl}amino)-naphthalene-5,6-diphosphonic acid;

carbonylbis-4-({4-[(4-aminopyrrole-1-methyl-2-carbonyl)amino]-1-methylpyrrole-2-carbonyl}amino)-naphthalene-2,5-diphosphonic acid;

carbonylbis-4-({4-[(4-aminopyrrole-1-methyl-2-carbonyl)amino]-1-methylpyrrole-2-carbonyl}amino)-naphthalene-6,7-diphosphonic acid;

carbonylbis-4-({4-[(4-aminopyrrole-1-methyl-2-carbonyl)amino]-1-methylpyrrole-2-carbonyl}amino)-naphthalene-2,6-diphosphonic acid;

carbonylbis-4-({4-[(4-aminopyrrole-1-methyl-2carbonyl)amino]-1-methylpyrrole-2-carbonyl}amino)-naphthalene-2,7-diphosphonic acid;

carbonylbis-1-({4-[(4-aminopyrrole-1-methyl-2-carbonyl)amino]-1-methylpyrrole-2-carbonyl}amino)-naphthalene-5-phosphonic acid;

carbonylbis-4-({4-[(4-aminopyrrole-1-methyl-2-carbonyl)amino]-1-methylpyrrole-2-carbonyl}amino)-naphthalene-5-phosphonic acid;

carbonylbis-4-({4-[(4-aminopyrrole-1-methyl-2-carbonyl)amino]-1-methylpyrrole-2-carbonyl}amino)-naphthalene-6-phosphonic acid; carbonylbis-1-({4-[(4-aminopyrrole-1-methyl-2-carbonyl)amino]-1-methylpyrrole-2-carbonyl}amino)-naphthalene-6-phosphonic acid;

carbonylbis-4-({4-[(4-aminopyrrole-1-methyl-2-carbonyl)amino]-1-methylpyrrole-2-carbonyl}amino)-naphthalene-2,5,6-triphosphonic acid;

carbonylbis-4-({4-[(4-aminopyrrole-1-methyl-2-carbonyl)amino]-1-methylpyrrole-2-carbonyl}amino)-naphthalene-1,5,7-triphosphonic acid;

carbonylbis-3-({4-[(4-aminopyrrole-1-methyl-2-carbonyl)amino]-1-methylpyrrole-2-carbonyl}amino)-naphthalene-1,5,7-triphosphonic acid;

carbonylbis-3-{[4-({4-[(4-aminopyrrole-1-methyl-2-carbonyl)amino]-1-methylpyrrole-2-carbonyl}amino)-1-methylpyrrole-2-carbonyl]amino}naphthalene-1,5-diphosphonic acid;

carbonylbis-4-{[4-({4-[(4-aminopyrrole-1-methyl-2-carbonyl)amino]-1-methylpyrrole-2-carbonyl}amino)-1-methylpyrrole-2-carbonyl]amino}-naphthalene-1,7-diphosphonic acid;

carbonylbis-1-{[4-({4-[(4-aminopyrrole-1-methyl-2-carbonyl)amino]-1-methylpyrrole-2-carbonyl}amino)-1-methylpyrrole-2-carbonyl]amino}-naphthalene-5,7-diphosphonic acid;

carbonylbis-4-{[4-({4-[(4-aminopyrrole-1-methyl-2-carbonyl)amino]-1-methylpyrrole-2-carbonyl}amino)-1-methylpyrrole-2-carbonyl]amino}-naphthalene-5,7-diphosphonic acid; and carbonylbis-3-{[4-({4-[(4-aminopyrrole-1-methyl-2-carbonyl)amino]-1-methylpyrrole-2-carbonyl}amino)-1-methylpyrrole-2-carbonyl]amino}-naphthalene-1,5,7-triphosphonic acid; and the $C_1$–$C_6$ alkyl and phenyl-$C_1$–$C_6$ alkyl esters and the pharmaceutically acceptable salts thereof.

4. A pharmaceutical composition comprising a pharmaceutically acceptable carrier and/or diluent and, as an active compound, a compound of formula (I) according to claim 1, or a pharmaceutically acceptable salt thereof.

5. A pharmaceutical composition comprising a pharmaceutically acceptable carrier and/or diluent and, as an active compound, the compound of claim 3, or a pharmaceutically acceptable salt thereof.

6. The compound of claim 1, wherein said compound is:
carbonylbis-3-({4-[(4-aminopyrrole-1-methyl-2-carbonyl)amino]-1-methylpyrrole-2-carbonyl}amino)-naphthalene-1,5-diphosphonic acid or a pharmaceutically acceptable salt thereof.

7. The compound of claim 1, wherein said compound is:
carbonylbis-4-({4-[(4-aminopyrrole-1-methyl-2-carbonyl)amino]-1-methylpyrrole-2-carbonyl}amino)-naphthalene-1,7-diphosphonic acid or a pharmaceutically acceptable salt thereof.

8. The compound of claim 1, wherein said compound is:
carbonylbis-3-{[4-({4-[(4-aminopyrrole-1-methyl-2-carbonyl)amino]-1-methylpyrrole-2-carbonyl}amino)-1-methylpyrrole-2-carbonyl]amino}naphthalene-1,5-diphosphonic acid or a pharmaceutically acceptable salt thereof.

9. The compound of claim 1, wherein said compound is:
carbonylbis-4-{[4-({4-[(4-aminopyrrole-1-methyl-2carbonyl)amino]-1-methylpyrrole-2-carbonyl}amino)-1-methylpyrrole-2-carbonyl]amino}-naphthalene-1,7-diphosphonic acid or a pharmaceutically acceptable salt thereof.

10. A method of protecting cells against the virus-induced cytopathic effects of HIV virus, comprising contacting said virus in the presence of said cells with an effective amount of a compound as set forth in claim 1.

11. A method of protecting cells against the virus-induced cytopathic effects of HIV virus, comprising contacting said virus in the presence of said cells with an effective amount of a compound as set forth in claim 2.

12. A method of protecting cells against the virus-induced cytopathic effects of HIV virus, comprising contacting said virus in the presence of said cells with an effective amount of a compound as set forth in claim 3.

13. A method of protecting cells against the virus-induced cytopathic effects of HIV virus, comprising contacting said virus in the presence of said cells with an effective amount of a compound as set forth in claim 6.

14. A method of protecting cells against the virus-induced cytopathic effects of HIV virus, comprising contacting said virus in the presence of said cells with an effective amount of a compound as set forth in claim 7.

15. A method of protecting cells against the virus-induced cytopathic effects of HIV virus, comprising contacting said virus in the presence of said cells with an effective amount of a compound as set forth in claim 8.

16. A method of protecting cells against the virus-induced cytopathic effects of HIV virus, comprising contacting said virus in the presence of said cells with an effective amount of a compound as set forth in claim 9.

* * * * *